(12) United States Patent
Almalki et al.

(10) Patent No.: US 11,371,914 B2
(45) Date of Patent: Jun. 28, 2022

(54) AUTOMATED HYDROGEN SULFIDE SAMPLER

(71) Applicant: Saudi Arabian Oil Company, Dhahran (SA)

(72) Inventors: Bandar Almalki, Dhahran (SA); Ali E. Aldossary, Dhahran (SA); Mohammed Aldaif, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 330 days.

(21) Appl. No.: 16/568,054

(22) Filed: Sep. 11, 2019

(65) Prior Publication Data

US 2021/0072120 A1 Mar. 11, 2021

(51) Int. Cl.
*G01N 1/20* (2006.01)
*G01N 1/18* (2006.01)

(52) U.S. Cl.
CPC ............ *G01N 1/2035* (2013.01); *G01N 1/18* (2013.01); *G01N 2001/205* (2013.01)

(58) Field of Classification Search
CPC .. G01N 1/2035; G01N 1/18; G01N 2001/205; G01N 2001/002; G01N 2001/2071; G01N 1/2247
USPC ...... 73/863.86, 863.01, 863.31, 864, 864.34, 73/864.51, 864.63, 864.73, 864.81
See application file for complete search history.

(56) References Cited

U.S. PATENT DOCUMENTS

| | | | |
|---|---|---|---|
| 5,473,952 A * | 12/1995 | Lieberman | G01N 1/12 73/863.01 |
| 7,866,222 B2 | 1/2011 | Moore et al. | |
| 8,686,364 B1 | 4/2014 | Little, III et al. | |
| 9,244,047 B2 | 1/2016 | Selman et al. | |
| 10,156,516 B2 | 12/2018 | Humblot et al. | |
| 2008/0047370 A1 | 2/2008 | Vickery, Jr. | |
| 2008/0098827 A1* | 5/2008 | Campbell | G01N 1/2035 73/863 |

(Continued)

FOREIGN PATENT DOCUMENTS

| | | |
|---|---|---|
| AU | 2004298634 B2 | 6/2005 |
| CN | 204101337 U | 1/2015 |

(Continued)

OTHER PUBLICATIONS

International Search Report and Written Opinion for related PCT application PCT/US2020/050282, dated Dec. 8, 2020.

*Primary Examiner* — Robert R Raevis
(74) *Attorney, Agent, or Firm* — Bracewell LLP; Constance G. Rhebergen; Linda L. Morgan

(57) ABSTRACT

A hydrogen sulfide sampler system for sampling for hydrogen sulfide in a fluid flow line includes a main tank in fluid communication with a fluid sample inlet line and a fluid sample outlet line. A plurality of sample bottles are in fluid communication with the main tank by way of the fluid sample outlet line. A drain tank is in fluid communication with the main tank by way of the fluid sample outlet line. A manifold assembly includes the fluid sample outlet line, the manifold assembly located between the main tank and the drain tank and further located between the main tank and the plurality of sample bottles. A return line is in fluid communication with the drain tank. An analysis system is operable to analyze a composition of a sample fluid contained within the main tank.

19 Claims, 2 Drawing Sheets

(56) References Cited

U.S. PATENT DOCUMENTS

2018/0340896 A1  11/2018  Briden et al.

FOREIGN PATENT DOCUMENTS

| | | |
|---|---|---|
| CN | 104764632 A | 7/2015 |
| WO | 02086455 A1 | 10/2002 |
| WO | 2018078609 A1 | 5/2018 |
| WO | 2018197040 A1 | 11/2018 |

* cited by examiner

AUTOMATED HYDROGEN SULFIDE SAMPLER

BACKGROUND OF THE DISCLOSURE

1. Field of the Disclosure

The present disclosure relates to testing a flow of fluids through a pipeline and in particular, to testing for and collecting samples of fluids having amounts of hydrogen sulfide.

2. Description of the Related Art

During hydrocarbon development operations some subterranean wells can be identified as producing fluids that contain hydrogen sulfide. In certain instances, such subterranean wells can have high levels of hydrogen sulfide. A subterranean well with a high level of hydrogen sulfide can be considered a well with a hydrogen sulfide level that exceeds 10% of the wellbore fluids. A subterranean well with an ultra-high level of hydrogen sulfide can be considered a well with a hydrogen sulfide level that exceeds 20% of the wellbore fluids. The release of the fluids containing hydrogen sulfide could be catastrophic for health, safety, and environmental reasons.

Produced fluids from subterranean wells can be tested to determine the level of hydrogen sulfide within such produced fluids. Current methods of testing fluids in a pipeline include using a full cascade system with a dragger tube at choke manifold assembly sampling points. Other alternate sampling methods can include utilizing closed chamber sampling bottles for collecting samples at the separator to send to a laboratory for further analysis.

SUMMARY OF THE DISCLOSURE

In some current systems that utilize dragger tubes, the amount of hydrogen sulfide in environments with high levels of hydrogen sulfide is not obtainable, or if obtained, the amount cannot be relied upon as being accurate. In addition, when taking closed samples at a choke are required, human intervention creates increased safety risks. In such situations, personnel with full self-contained breathing apparatus are placed in a potentially harmful situation. If collecting a sample at the separator, the fluid must be flowing at a sufficient rate over a sufficient time for the sampling to be successful.

Systems and methods of this disclosure provide for sampling fluids with high levels of hydrogen sulfide remotely so that the risk to personnel and operators is reduced and limited. In addition the flow rate of the fluid can be at any level and the sample simple can still function to obtain samples as needed.

Embodiments of the current application provide systems and method for a sample to be obtained from a flow line at a sample port and stored in a main tank. The sample can be analyzed at the main tank to obtain a hydrogen sulfide reading. After the hydrogen sulfide reading has been obtained, a decision can be made whether or not to dump the sample or store the sample in a sampling bottle. If sample the sample is to be dumped, the sample will be flushed back into the flow line downstream from the sample port where the sample was obtained. A pump can be used for flushing main tank and the dump tank. All of these steps can be performed remotely without direct human contact at the location where the samples are obtained. Component of the system can be contained within a sealed box and hydrogen sulfide sensors can be used to detect a leak of hydrogen sulfide so that the sealed box can be safely transported to a laboratory.

In an embodiment of this disclosure, a hydrogen sulfide sampler system for sampling for hydrogen sulfide in a fluid flow line includes a main tank in fluid communication with a fluid sample inlet line and a fluid sample outlet line. A plurality of sample bottles are in fluid communication with the main tank by way of the fluid sample outlet line. A drain tank is in fluid communication with the main tank by way of the fluid sample outlet line. A manifold assembly includes the fluid sample outlet line. The manifold assembly is located between the main tank and the drain tank and is further located between the main tank and the plurality of sample bottles. A return line is in fluid communication with the drain tank. An analysis system is operable to analyze a composition of a sample fluid contained within the main tank.

In alternate embodiments, a sensor unit can be operable to sense a leak of hydrogen sulfide out of the system and to identify an operational status of the system. The manifold assembly can further include a plurality of needle valves. The plurality of needle valves can be operable to move from a closed position to an open position to direct a fluid sample towards one of the plurality of sample bottles or the drain tank. The plurality of needle valves can be operated remotely from a location spaced physically apart from the manifold assembly. A control system can be operable to instruct each of the plurality of needle valves to move between the closed position and the open position.

In other alternate embodiments, an inlet shutoff valve can be located along the fluid sample inlet line. An outlet shutoff valve can be located along the return line. A pump can be operable to pressurize the sample fluid contained within the main tank. A pump can be operable to pressurize a drain fluid contained within the drain tank.

In an alternate embodiment of this disclosure, a hydrogen sulfide sampler system for sampling for hydrogen sulfide in a fluid flow line includes a main tank. A fluid sample inlet line extends between a sample port of the fluid flow line and the main tank. An inlet shutoff valve is located along the fluid sample inlet line. A fluid sample outlet line extends from the main tank. A plurality of sample bottles are in fluid communication with the main tank by way of the fluid sample outlet line. A drain tank is in fluid communication with the main tank by way of the fluid sample outlet line. A manifold assembly includes the fluid sample outlet line. The manifold assembly is located between the main tank and the drain tank and further located between the main tank and the plurality of sample bottles. A return line extends between the drain tank and a return port of the fluid flow line. An outlet shutoff valve is located along the return line. An analysis system is operable to analyze a composition of a sample fluid contained within the main tank.

In yet another alternate embodiment of this disclosure, a method for sampling a fluid for hydrogen sulfide in a fluid flow line with a hydrogen sulfide sampler system includes connecting a fluid sample inlet line of the hydrogen sulfide sampler system to a sample port of the fluid flow line. A return line of the hydrogen sulfide sampler system is connected to a return port of the fluid flow line. The hydrogen sulfide sampler system further includes a main tank in fluid communication with the fluid sample inlet line and a fluid sample outlet line. A plurality of sample bottles is in fluid communication with the main tank by way of the fluid sample outlet line. A drain tank is in fluid communication with the main tank by way of the fluid sample outlet line. A manifold assembly includes the fluid sample outlet line. The manifold assembly is located between the main tank and the drain tank, and is further located between the main tank and the plurality of sample bottles. The return line is in fluid communication with the drain tank. Hydrogen sulfide sampler system further includes an analysis system. The method further includes analyzing a composition of a sample fluid contained within the main tank with the analysis system.

In alternate embodiments, a leak of hydrogen sulfide out of the system can be sensed with a sensor unit and an operational status of the system can be identified with the sensor unit. The manifold assembly can further include a plurality of needle valves, and the method can further include moving at least one of the plurality of needle valves from a closed position to an open position to direct a fluid sample towards one of the plurality of sample bottles or the drain tank. The plurality of needle valves can be remotely operated from a location spaced physically apart from the manifold assembly. Each of the plurality of needle valves can be instructed to move between the closed position and the open position with a control system.

In other alternate embodiments, the method can further include moving an inlet shutoff valve from a closed position to an open position to fill the main tank with a fluid sample from the fluid flow line. The inlet shutoff valve can be located along the fluid sample inlet line. An outlet shutoff valve can be opened to return a drain fluid from the drain tank to the fluid flow line. The outlet shutoff valve can be located along the return line. The sample fluid contained within the main tank can be pressurized with a pump. A drain fluid contained within the drain tank can be pressurized with a pump.

BRIEF DESCRIPTION OF THE DRAWINGS

So that the manner in which the features, aspects and advantages of the embodiments of this disclosure, as well as others that will become apparent, are attained and can be understood in detail, a more particular description of the disclosure may be had by reference to the embodiments thereof that are illustrated in the drawings that form a part of this specification. It is to be noted, however, that the appended drawings illustrate only certain embodiments of the disclosure and are, therefore, not to be considered limiting of the disclosure's scope, for the disclosure may admit to other equally effective embodiments.

DETAILED DESCRIPTION

The disclosure refers to particular features, including process or method steps. Those of skill in the art understand that the disclosure is not limited to or by the description of embodiments given in the specification. The subject matter of this disclosure is not restricted except only in the spirit of the specification and appended Claims.

Those of skill in the art also understand that the terminology used for describing particular embodiments does not limit the scope or breadth of the embodiments of the disclosure. In interpreting the specification and appended Claims, all terms should be interpreted in the broadest possible manner consistent with the context of each term. All technical and scientific terms used in the specification and appended Claims have the same meaning as commonly understood by one of ordinary skill in the art to which this disclosure belongs unless defined otherwise.

As used in the Specification and appended Claims, the singular forms "a", "an", and "the" include plural references unless the context clearly indicates otherwise.

As used, the words "comprise," "has," "includes", and all other grammatical variations are each intended to have an open, non-limiting meaning that does not exclude additional elements, components or steps. Embodiments of the present disclosure may suitably "comprise", "consist" or "consist essentially of" the limiting features disclosed, and may be practiced in the absence of a limiting feature not disclosed. For example, it can be recognized by those skilled in the art that certain steps can be combined into a single step.

Where a range of values is provided in the Specification or in the appended Claims, it is understood that the interval encompasses each intervening value between the upper limit and the lower limit as well as the upper limit and the lower limit. The disclosure encompasses and bounds smaller ranges of the interval subject to any specific exclusion provided.

Where reference is made in the specification and appended Claims to a method comprising two or more defined steps, the defined steps can be carried out in any order or simultaneously except where the context excludes that possibility.

Figure 1:
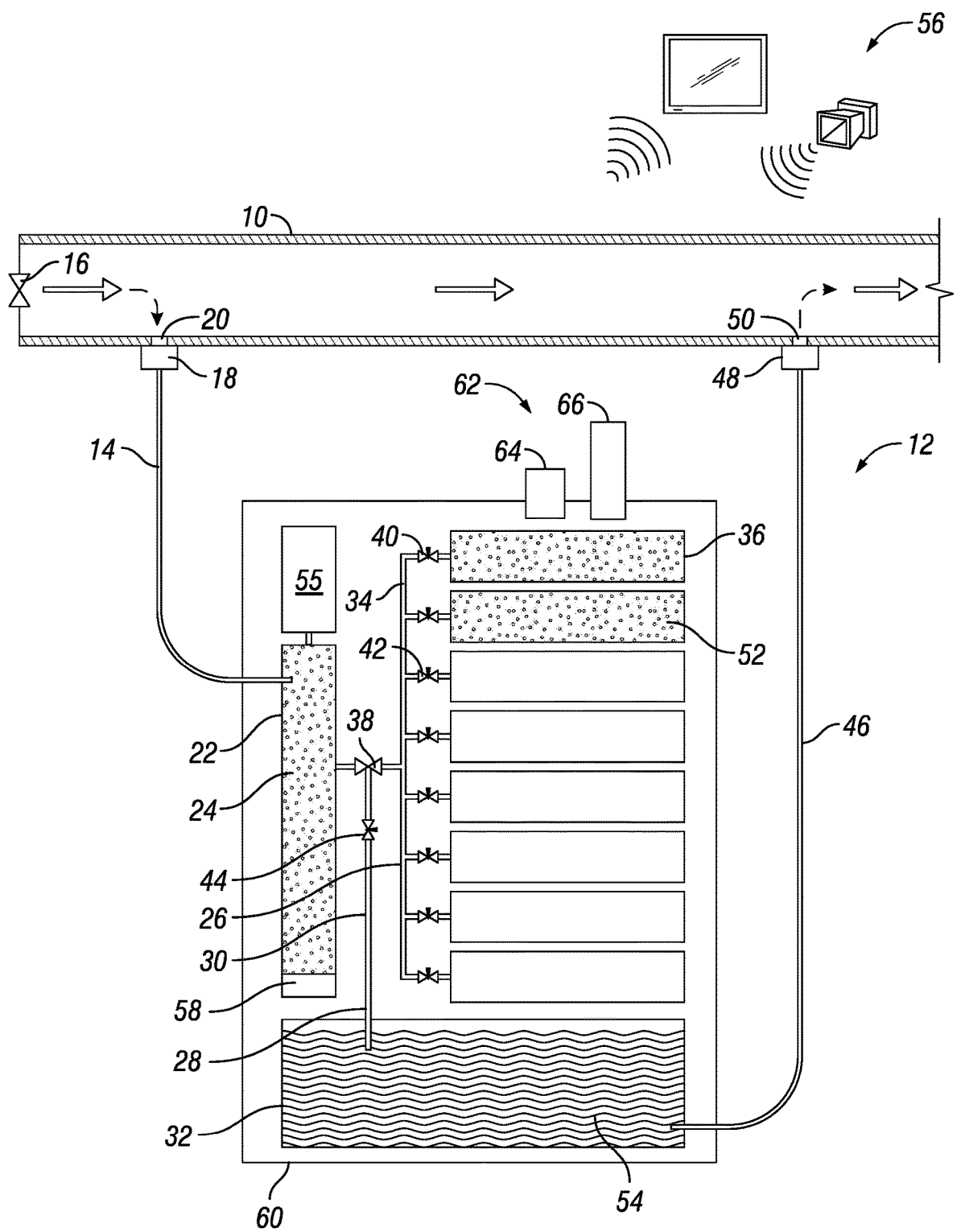
FIG. 1 is a schematic section view of a hydrogen sulfide sampler system for sampling for hydrogen sulfide, in accordance with an embodiment of this disclosure.

Looking at FIG. 1, fluid flow line 10 can transport a flow of fluids associated with hydrocarbon development. Fluid flow line 10 can transport a flow of fluid that contains a liquid, a gas, or a combination of liquid and gas. The flow of fluid through fluid flow line 10 can contain hydrogen sulfide. Although embodiments of this disclosure are directed to sampling for hydrogen sulfide, systems and methods can include additional or alternate sensors that can allow for the measuring of other substances. Systems and methods of this disclosure provide automated hydrogen sulfide sampler system 12 for sampling for hydrogen sulfide in fluid flow line 10.

Hydrogen sulfide sampler system 12 includes fluid sample inlet line 14. Fluid sample inlet line 14 connects to fluid flow line 10 downstream of choke 16. Choke 16 can be used to control the pressure and flow rate of the fluid flowing through fluid flow line 10, before the fluid reaches sample port 20. Fluid sample inlet line 14 includes inlet shutoff valve 18 that is located along fluid sample inlet line 14. Inlet shutoff valve 18 can be automatically operated with a contingent manual mechanism to close. When inlet shutoff valve 18 is in the closed position fluid that is flowing through fluid flow line 10 is prevented from passing through fluid sample inlet line 14. When inlet shutoff valve 18 is in the open position a portion of the fluid that is flowing through fluid flow line 10 can pass through fluid sample inlet line 14.

In the example of FIG. 1, inlet shutoff valve 18 is located at sample port 20. Sample port 20 is an opening that extends through a sidewall of fluid flow line 10. Main tank 22 is in fluid communication with fluid sample inlet line 14. In the Example of FIG. 1, fluid sample inlet line 14 connects to sample port 20 and extends between sample port 20 of fluid flow line 10 and main tank 22.

In order to direct a portion a portion of the fluid that is flowing through fluid flow line 10, inlet shutoff valve 18 can be moved from a closed position to an open position so that the portion of fluid can pass through fluid sample inlet line 14 and into main tank 22. With inlet shutoff valve 18 in the open position, main tank 22 will in this way be filled with sample fluid 24. Sample fluid 24 is the portion of the fluid that was flowing through fluid flow line 10 that passed through inlet shutoff valve 18, through fluid sample inlet line 14 and into main tank 22.

Main tank 22 can contain a volume of sample fluid 24 in a range of five to thirty gallons. After a sufficient volume of sample fluid 24 is contained within main tank 22, inlet shutoff valve 18 can be moved from the open position to the closed position. In the closed position, no part of the fluid that is flowing through fluid flow line 10 can pass through inlet shutoff valve 18 into fluid sample inlet line 14.

Main tank 22 can also be in fluid communication with manifold assembly 26 that directs fluid exiting main tank 22. Manifold assembly 26 includes fluid sample outlet line 28. Fluid sample outlet line 28 can include flow line branches that extend from main tank 22. Fluid sample outlet line 28 includes drain outlet line 30. Drain outlet line 30 extends from main tank 22 to drain tank 32 so that main tank 22 is in fluid communication with drain tank 32 by way of fluid sample outlet line 28. Bottles outlet line 34 extends from main tank 22 to each of a plurality of sample bottles 36 so that main tank 22 is in fluid communication with each of the sample bottles 36 by way of fluid sample outlet line 28. Sample bottles 36 are individual storage containers that can be used to store fluid from main tank 22. In the example embodiment of FIG. 1, there are eight sample bottles 36 shown. In alternate examples, there may be as few as one sample bottle 36 or more than eight sample bottles 36. In an example embodiment, sample bottles 36 can have a rating of 15,000 psi.

The components of manifold assembly 26 are located between main tank 22 and drain tank 32. The components of manifold assembly 26 are further located between main tank 22 and sample bottles 36. The components of manifold assembly 26 can operate to direct sample fluid 24 that is exiting main tank 22 towards drain tank 32 or one or more of the sample bottles 36.

Manifold assembly 26 can include outlet valve 38. Outlet valve 38 is located at an outlet of main tank 22. When outlet valve 38 is in a closed position, no fluid within main tank 22 can exit out of main tank 22 through outlet valve 38. When outlet valve 38 is in an open position, fluid within main tank 22 can exit out of main tank 22 through outlet valve 38 and be directed towards drain tank 32 or one or more of the sample bottles 36.

Manifold assembly 26 can further include a plurality of needle valves 40. Certain of the needle valves 40 are sample needle valves 42 that are associated with a sample bottle 36. By moving sample needle valves 42 between an open position and a closed position, fluids that are exiting main tank 22 can be directed into selected sample bottles 36. When a sample needle valve 42 associated with a certain sample bottle 36 is in an open position, fluids that are exiting main tank 22 can enter such sample bottle 36. Fluid that enters a sample bottle 36 is shown as bottle fluid 52. In the example embodiment of FIG. 1, two of the sample bottles 36 contain bottle fluid 52. In alternate embodiments, as few as none and as many as all sample bottles 36 can contain bottle fluid 52. When a sample needle valve 42 associated with a certain sample bottle 36 is in a closed position, fluids that are exiting main tank 22 cannot enter such sample bottle 36.

Another of the needle valves 40 is a drain needle valve 44. When drain needle valve 44 is in an open position, fluids that are exiting main tank 22 can enter drain tank 32. When drain needle valve 44 is in a closed position, fluids that are exiting main tank 22 cannot enter drain tank 32. Although each of the needle valves 40 are described as being a needle valve, each of such valves can be an alternate type of automated one way valve that can be operated remotely that is known in the industry. Fluid that enters drain tank 32 from main tank 22 is shown as drain fluid. 54. The purpose of drain tank 32 is to contain drain fluid 54, which is not being kept for further analyses, but will be flushed out of hydrogen sulfide sampler system 12 and back into fluid flow line 10.

Hydrogen sulfide sampler system 12 further includes return line 46. Return line 46 is in fluid communication with drain tank 32. Return line 46 is connected to return port 50 of fluid flow line 10 and extends between drain tank 32 and return port 50.

Return line 46 includes outlet shutoff valve 48 that is located along return line 46 and can be an automated valve. When outlet shutoff valve 48 is in the closed position fluid is prevented from passing through outlet shutoff valve 48. When outlet shutoff valve 48 is in the open position fluid within hydrogen sulfide sampler system 12 can be returned to fluid flow line 10 through return line 46.

In the example of FIG. 1, outlet shutoff valve 48 is located at return port 50. Return port 50 is an opening that extends through a sidewall of fluid flow line 10. Drain tank 32 is in fluid communication with return line 46. In the Example of FIG. 1, return line 46 connects to return port 50 and extends between return port 50 of fluid flow line 10 and drain tank 32.

In order to direct a fluid that is within drain tank 32 out of hydrogen sulfide sampler system 12, outlet shutoff valve 48 can be moved from a closed position to an open position so that fluid is drained from drain tank 32 and can pass through return line 46 and into fluid flow line 10. After drain tank 32 has been sufficiently flushed, outlet shutoff valve 48 can be returned to a closed position.

Pump 55 can be used to help move sample fluid 24 out of main tank 22. Pump 55 can pressurize sample fluid 24 contained within main tank 22, forcing sample fluid 24 out of main tank 22 and into fluid sample outlet line 28. Pump 55 can also be used to move drain fluid 54 out of drain tank 32. Pump 55 can pressurize drain fluid 54 contained within drain tank 32, forcing drain fluid 54 out of drain tank 32 and into return line 46. In the example embodiment of FIG. 1, pump 55 can pressurize both sample fluid 24 contained within main tank 22 and drain fluid 54 contained within drain tank 32. In alternate embodiments, pump 55 can pressurize sample fluid 24 contained within main tank 22 and a separate pump can pressurize drain fluid 54 contained within drain tank 32.

Each of the needle valves 40, as well as inlet shutoff valve 18, outlet valve 38, and outlet shutoff valve 48 can be remotely operated. As an example, each of the needle valves 40, and outlet valve 38 can be operated remotely from a location spaced physically apart from manifold assembly 26. In addition, each of the needle valves 40, as well as inlet shutoff valve 18, outlet valve 38, and outlet shutoff valve 48 can be operated by an operator who is located at a physical location that is mechanically and physically spaced apart from fluid flow line 10.

Control system 56 can be used for the remote operation of each of the needle valves 40, as well as inlet shutoff valve 18, outlet valve 38, drain needle valve 44, and outlet shutoff valve 48 and for providing communication between the local components of the hydrogen sulfide sampler system 12 that are located in mechanical connection with fluid flow line 10, and the remote components of the hydrogen sulfide sampler system 12 that are located mechanically and physically separate from fluid flow line 10. Control system 56 can include a control panel and can be powered by an electrical power source, or with batteries. Control system 56 can be operated wirelessly from a remote location that is spaced physically apart from control system 56.

As an example, control system 56 can be used to remotely operate needle valves 40 from a location spaced physically apart from manifold assembly 26. Control system 56 can be used, for example, to instruct each of the needle valves 40 to move between the closed position and the open position for directing fluids that exit main tank 22 towards drain tank 32 or one or more of the sample bottles 36. An operator can provide pre-set values for instructing the operation or control system 56. The operator can override or adjust such pre-set values during operation of hydrogen sulfide sampler system 12, as needed.

Analysis system 58 can analyze a composition of sample fluid 24 contained within main tank 22. Analysis system 58 can more specifically determine an amount of hydrogen sulfide within sample fluid 24. Analysis system 58 can also be in contact with control system 56 so that a status of the analysis operation, as well as analytical results can be available to an operator.

After initial analysis of sample fluid 24 is complete, a decision can be made to either send the sample fluid 24 to the drain tank 32 to be drained from hydrogen sulfide sampler system 12, or send the sample fluid 24 to one or more of the sample bottles 36 so that the fluid can be saved for transport back to a laboratory for further testing. The determination to send sample fluid 24 to a sample bottle 36 for transport back to a laboratory can be made if it is determined that a well owner or operator wants or needs additional analysis performed.

Each of the main tank 22, drain tank 32, manifold assembly 26, sample bottles 36, and pump 55, can be contained within case 60, which is depicted schematically in FIG. 1 by dashed lines. Case 60 can form a sealed unit so that any leaks of the components within case 60 would be sealed from the environment. Case 60 can be used to safely transport bottle fluid 52 within sample bottles 36 back to a laboratory where bottle fluid 52 can be further tested in a controlled environment. Case 60 can be sized and shaped so that hydrogen sulfide sampler system 12 can be a mobile unit that is easily moveable between various work sites and a laboratory.

In order to assist in maintaining a safe working environment, sensor unit 62 can be mounted on case 60. Sensor unit 62 can include a leak detector 64 that can detect a leak of hydrogen sulfide out of hydrogen sulfide sampler system 12. When a leak of hydrogen sulfide is detected leak detector 64 can emit a visual alarm or audible alarm, or both a visual and audible alarm locally or through control system 56, or both locally and through control system 56.

Sensor unit 62 can further include status identifier 66. Status identifier 66 can provide a visual or audible indication of the operational status of hydrogen sulfide sampler system 12. As an example, when hydrogen sulfide sampler system 12 is actively operating, status identifier 66 can provide a visual indication, such as a colored light locally. Status identifier 66 can provide a visual indication, such as a colored light locally. Status identifier 66 can further provide an operational status of hydrogen sulfide sampler system 12 through control system 56.

Figure 2:
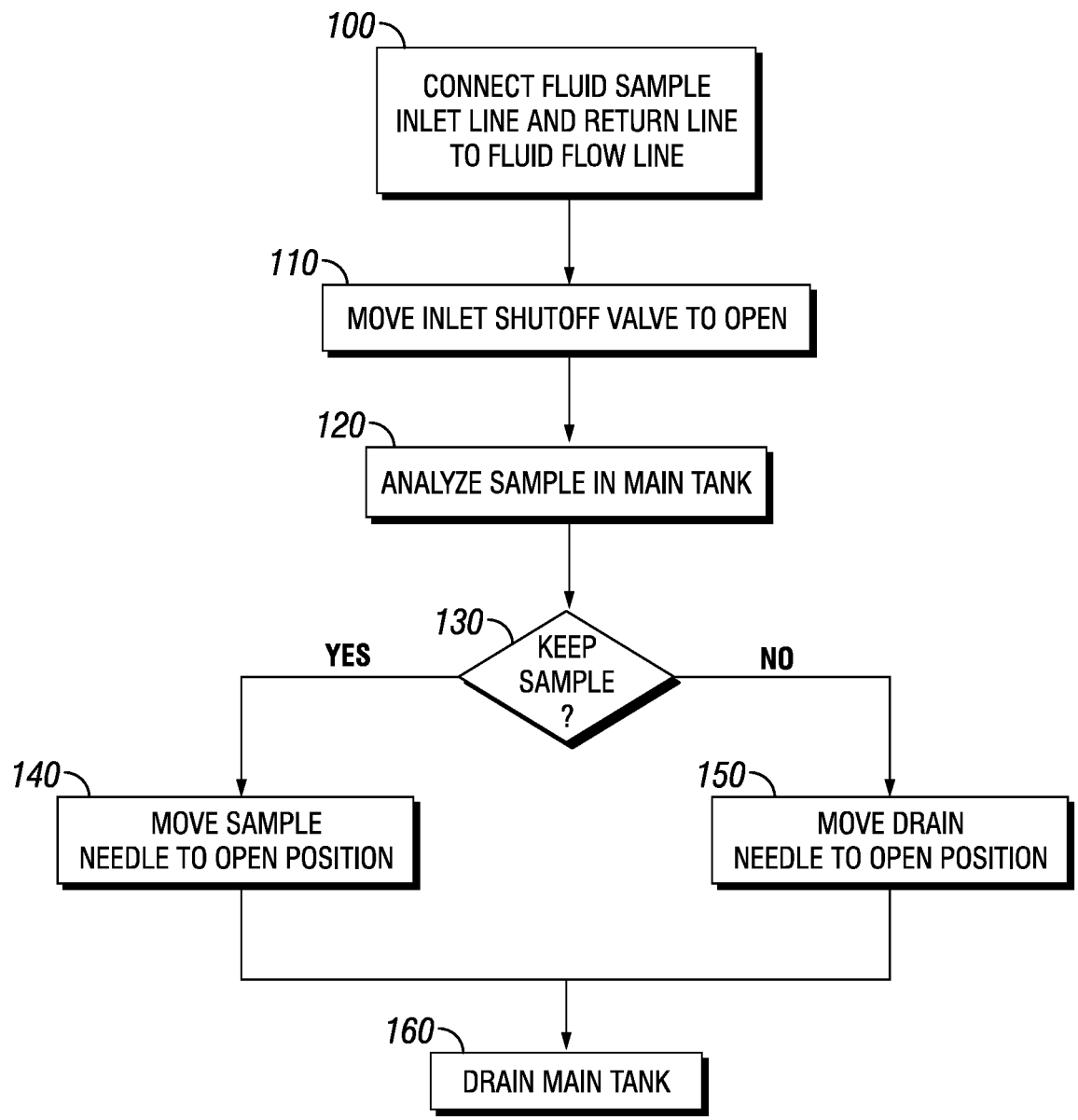
FIG. 2 is a schematic flow diagram illustrating a method of sampling a fluid for hydrogen sulfide in a fluid flow line with a hydrogen sulfide sampler system, in accordance with an embodiment of this disclosure.

Looking at FIG. 2, in an example of operation, in step 100, fluid sample inlet line 14 and return line 46 are connected to fluid flow line 10 at sampling ports downstream of choke 16. When 14 and 16 are connected to fluid flow line 10, inlet shutoff valve 18 and outlet shutoff valve 48 are both in the closed position. In step 110, inlet shutoff valve 18 is moved from the closed position to the open position so that a portion of the fluid traveling through fluid flow line 10 is directed into main tank 22. In step 120, the sample fluid 24 within main tank 22 is analyzed by analysis system 58 to determine the level of hydrogen sulfide within sample fluid 24.

After sample fluid 24 is analyzed, a decision is made in step 130 whether or not to drain sample fluid 24 back into fluid flow line 10, or store sample fluid 24 within sample bottles 36. In step 130, if sample fluid 24 is to be stored in one or more of the sample bottles 36, in step 140, manifold assembly 26 is remotely operated to open sample needle valve 42 associated with the sample bottle 36 in which the sample is to be stored. Pump 55 can be used to move the fluid into sample bottle 36. Any remaining sample fluid 24 can then be flushed into drain tank 32, as described below in the same way as described for step 150.

In step 130, if sample fluid 24 is to be dumped and flushed back into fluid flow line 10, then in step 150 manifold assembly 26 is remotely operated to open drain needle valve 44. Pump 55 can be used to move the fluid from main tank 22 into drain tank 32.

In step 160, regardless of whether or not any of sample fluid 24 was stored in sample bottle 36, main tank 22 can then be drained and flushed. Pump 55 can be used to drain and flush both main tank 22 and drain tank 32. Main tank 22 and drain tank 32 can be flushed by pumping a different fluid through fluid flow line 10 and into and through main tank 22 into drain tank 32. When flushing main tank 22 and drain tank 32, outlet shutoff valve 48 is moved to the open position so that the fluids in main tank 22 and drain tank 32 can be flushed back into fluid flow line 10.

After completion of the flushing of main tank 22 and drain tank 32, inlet shutoff valve 18 and outlet shutoff valve 48 can be in or moved to the closed position. Hydrogen sulfide sampler system 12 can then be disconnected from fluid flow line 10. If samples were stored in sample bottles 36, hydrogen sulfide sampler system 12 can be transported to a laboratory so that the bottle fluid 52 can undergo further testing. The further testing can include analyzing the composition of the gas or oil, performing a pressure, volume and temperature test, performing a depletion test, performing a separator test, performing a viscosity test, or performing any combination of such tests.

Embodiments described in this disclosure therefore can provide a system for testing wells with high levels of hydrogen sulfide that allows for accurate results over a range of flow rates. No direct human intervention is required at the test site. Samples that are stored in internal bottles can be safely transported in a closed system to a laboratory for further testing. During the sampling, analyzing, and storing procedure the samples are not exposed to the atmosphere.

Embodiments of this disclosure, therefore, are well adapted to carry out the objects and attain the ends and advantages mentioned, as well as others that are inherent. While embodiments of the disclosure has been given for purposes of disclosure, numerous changes exist in the details of procedures for accomplishing the desired results. These and other similar modifications will readily suggest themselves to those skilled in the art, and are intended to be encompassed within the spirit of the present disclosure and the scope of the appended claims.

What is claimed is:
1. A hydrogen sulfide sampler system for sampling for hydrogen sulfide in a fluid flow line, the system including:

a main tank in fluid communication with a fluid sample inlet line and a fluid sample outlet line;
a plurality of sample bottles in selective fluid communication with the main tank by way of the fluid sample outlet line;
a drain tank in selective fluid communication with the main tank by way of the fluid sample outlet line;
a manifold assembly that includes the fluid sample outlet line, the manifold assembly located between the main tank and the drain tank and further located between the main tank and the plurality of sample bottles, the manifold assembly operable to direct a sample fluid to one of the drain tank and the plurality of sample bottles;
a return line in fluid communication with the drain tank; and
an analysis system operable to analyze a composition of the sample fluid contained within the main tank.

2. The system of claim 1, further including a sensor unit, the sensor unit operable to sense a leak of hydrogen sulfide out of the system and to identify an operational status of the system.

3. The system of claim 1, where the manifold assembly further includes a plurality of needle valves, the plurality of needle valves operable to move from a closed position to an open position to direct a fluid sample towards one of the plurality of sample bottles or the drain tank.

4. The system of claim 3, where the plurality of needle valves are operated remotely from a location spaced physically apart from the manifold assembly.

5. The system of claim 3, further including a control system operable to instruct each of the plurality of needle valves to move between the closed position and the open position.

6. The system of claim 1, further including an inlet shutoff valve, the inlet shutoff valve located along the fluid sample inlet line.

7. The system of claim 1, further including an outlet shutoff valve, the outlet shutoff valve located along the return line.

8. The system of claim 1, further including a pump operable to pressurize the sample fluid contained within the main tank.

9. The system of claim 1, further including a pump operable to pressurize a drain fluid contained within the drain tank.

10. A hydrogen sulfide sampler system for sampling for hydrogen sulfide in a fluid flow line, the system including:
a main tank;
a fluid sample inlet line extending between a sample port of the fluid flow line and the main tank;
an inlet shutoff valve located along the fluid sample inlet line;
a fluid sample outlet line extending from the main tank;
a plurality of sample bottles in selective fluid communication with the main tank by way of the fluid sample outlet line;
a drain tank in selective fluid communication with the main tank by way of the fluid sample outlet line;
a manifold assembly that includes the fluid sample outlet line, the manifold assembly located between the main tank and the drain tank and further located between the main tank and the plurality of sample bottles, the manifold assembly operable to direct a sample fluid to one of the drain tank and the plurality of sample bottles;
a return line extending between the drain tank and a return port of the fluid flow line;
an outlet shutoff valve located along the return line; and
an analysis system operable to analyze a composition of the sample fluid contained within the main tank.

11. A method for sampling a fluid for hydrogen sulfide in a fluid flow line with a hydrogen sulfide sampler system, the method including:
connecting a fluid sample inlet line of the hydrogen sulfide sampler system to a sample port of the fluid flow line;
connecting a return line of the hydrogen sulfide sampler system to a return port of the fluid flow line, where the hydrogen sulfide sampler system further includes:
a main tank in fluid communication with the fluid sample inlet line and a fluid sample outlet line;
a plurality of sample bottles in selective fluid communication with the main tank by way of the fluid sample outlet line;
a drain tank in selective fluid communication with the main tank by way of the fluid sample outlet line;
a manifold assembly that includes the fluid sample outlet line, the manifold assembly located between the main tank and the drain tank and further located between the main tank and the plurality of sample bottles;
the return line in fluid communication with the drain tank; and
an analysis system; where
the method further includes analyzing a composition of a sample fluid contained within the main tank with the analysis system; and
operating the manifold assembly to direct the sample fluid to one of the drain tank and the plurality of sample bottles.

12. The method of claim 11, further including sensing a leak of hydrogen sulfide out of the system and identifying an operational status of the system with a sensor unit.

13. The method of claim 11, where the manifold assembly further includes a plurality of needle valves, the method further including moving at least one of the plurality of needle valves from a closed position to an open position to direct a fluid sample towards one of the plurality of sample bottles or the drain tank.

14. The method of claim 13, further including remotely operating the plurality of needle valves from a location spaced physically apart from the manifold assembly.

15. The method of claim 13, further including instructing each of the plurality of needle valves to move between the closed position and the open position with a control system.

16. The method of claim 11, further including moving an inlet shutoff valve from a closed position to an open position to fill the main tank with a fluid sample from the fluid flow line, where the inlet shutoff valve is located along the fluid sample inlet line.

17. The method of claim 11, further including opening an outlet shutoff valve to return a drain fluid from the drain tank to the fluid flow line, where the outlet shutoff valve is located along the return line.

18. The method of claim 11, further including pressurizing the sample fluid contained within the main tank with a pump.

19. The method of claim 11, further including pressurizing a drain fluid contained within the drain tank with a pump.

* * * * *